United States Patent
Birnbach

(10) Patent No.: US 8,019,047 B2
(45) Date of Patent: Sep. 13, 2011

(54) FLASH X-RAY IRRADIATOR

(75) Inventor: Curtis A. Birnbach, New Rochelle, NY (US)

(73) Assignee: Advanced Fusion Systems LLC, Newtown, CT (US)

( * ) Notice: Subject to any disclaimer, the term of this patent is extended or adjusted under 35 U.S.C. 154(b) by 118 days.

(21) Appl. No.: 12/467,974

(22) Filed: May 18, 2009

(65) Prior Publication Data

US 2009/0285362 A1 Nov. 19, 2009

Related U.S. Application Data

(60) Provisional application No. 61/127,845, filed on May 16, 2008.

(51) Int. Cl.
*H01J 35/00* (2006.01)

(52) U.S. Cl. .......................... 378/122; 378/64; 378/106

(58) Field of Classification Search .................... 378/64, 378/66, 106, 119, 121, 122, 193
See application file for complete search history.

(56) References Cited

U.S. PATENT DOCUMENTS

| | | | |
|---|---|---|---|
| 2,984,751 A | 5/1961 | Cliborn | |
| 3,518,433 A * | 6/1970 | Owen | 378/106 |
| 3,527,942 A | 9/1970 | Roe et al. | |
| 4,151,419 A | 4/1979 | Morris et al. | |
| 4,396,580 A | 8/1983 | Patrick et al. | |
| 4,670,894 A | 6/1987 | Birnbach et al. | |
| 4,723,263 A | 2/1988 | Birnbach et al. | |
| 4,950,962 A | 8/1990 | Birnbach et al. | |
| 5,311,566 A | 5/1994 | Curry et al. | |
| 5,323,442 A | 6/1994 | Golovanivsky et al. | |
| 6,320,935 B1 | 11/2001 | Shinar et al. | |
| 6,405,701 B1 | 6/2002 | Masberg et al. | |
| 7,274,772 B2 | 9/2007 | Lesiak et al. | |
| 7,277,527 B2 | 10/2007 | Gallagher | |
| 7,447,298 B2 | 11/2008 | Busta et al. | |
| 2008/0063132 A1 | 3/2008 | Birnbach | |

OTHER PUBLICATIONS

Suess et al., Radiation Treatment of Sewage Sludge—Experience with an Operating Pilot Plant, Radiat. Phys, Chem, 1977, vol. 9, pp. 353-370, Pergamon Press, Great Britain.

* cited by examiner

*Primary Examiner* — Jurie Yun
(74) *Attorney, Agent, or Firm* — Bruzga & Associates; Charles E. Bruzga

(57) ABSTRACT

An apparatus for Flash X-ray irradiation of material includes a Flash X-ray source comprised of an electron gun and an anode. The electron gun comprises a field emission cold cathode having an electron emitting surface, and a grid for controlling electron flow from the cathode to the anode. The anode has an electron-receiving main surface and an X-ray emitting, oppositely facing main surface. The X-ray emitting surface, emits X-radiation into an irradiation volume. The X-ray emitting surface of the anode has orthogonally oriented first and second dimensions of greater than 2 millimeters each. A high voltage pulse power supply powers the Flash X-ray source. The electron gun, anode and high voltage pulse power supply are so constructed as to create sufficient X-radiation in said irradiation volume to achieve a desired level of irradiation of material in said volume.

17 Claims, 12 Drawing Sheets

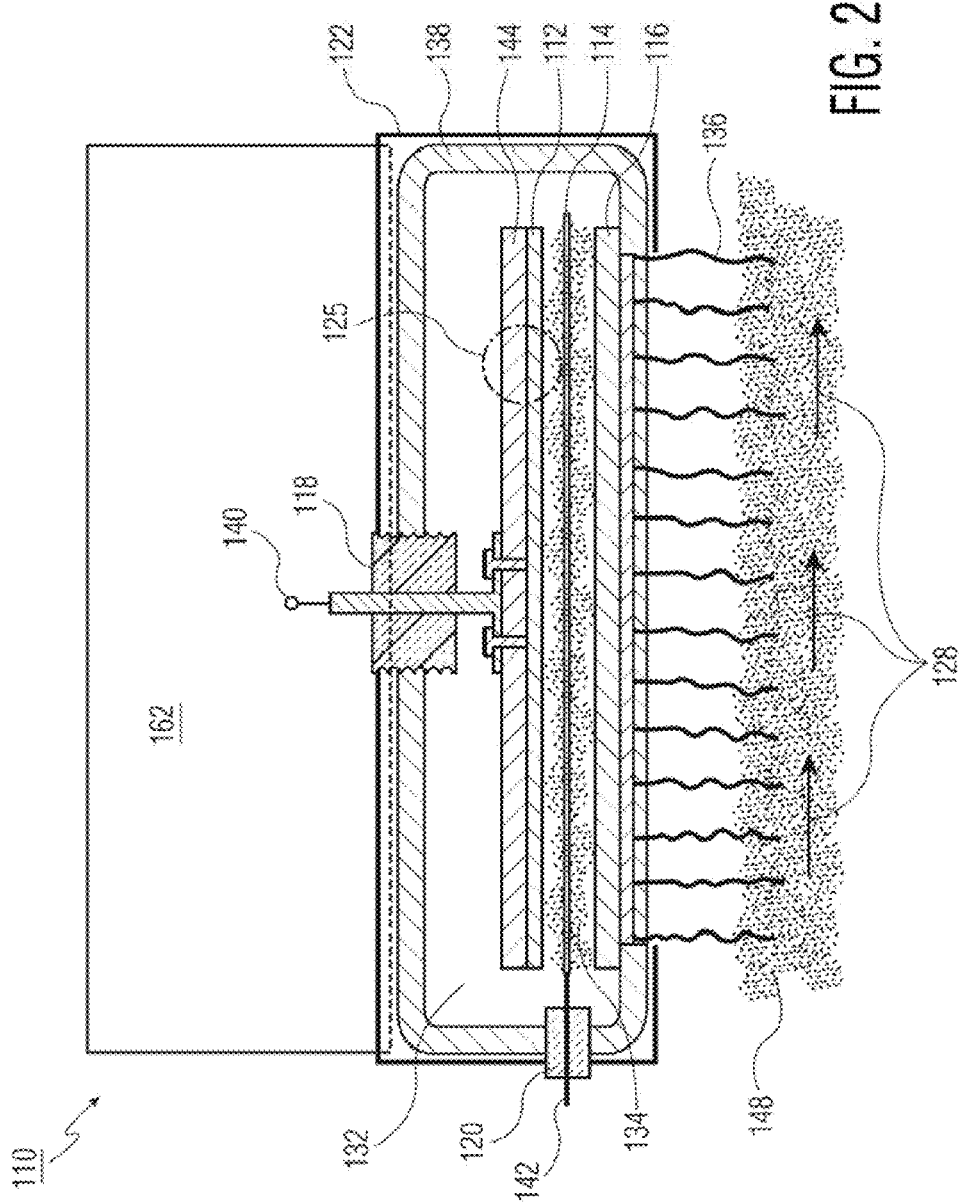

FLASH X-RAY IRRADIATOR

FIELD OF THE INVENTION

The present invention relates to apparatus for irradiation of materials. The invention relates more particularly to an apparatus that produces a high speed X-ray pulse or pulses for irradiation of materials.

BACKGROUND OF THE INVENTION

Sterilization of various materials by irradiation with high-energy radiation (gamma and X-ray) is a well-established technology. High-energy irradiation can break molecular bonds in various materials and decompose the toxic compounds into more benign compounds. Gamma sterilization has been considered the norm up until now because of the high energy and fluence (amount of radiation delivered per unit of time) of the source. Use of X-ray irradiation for manufacturing purposes such as the manufacture of heat-shrink tubing for electronics is also known.

For sterilization with gamma radiation, $^{60}$Cobalt has been the standard radioisotope of choice. $^{60}$Cobalt emits gamma rays at energies of 1.17 MeV and 1.33 MeV. The efficacy of radiation at these energies has been long established for these applications. One of the drawbacks to the use of $^{60}$Cobalt is that its higher energy line (1.33 MeV) is above the energy level at which radioactivity is induced. There is a need for an irradiation apparatus whose maximum energy output is below the threshold of $^{60}$Cobalt, so as to avoid the problem of inducing radioactivity in material being irradiated. It would further be desirable to provide an apparatus for irradiation that altogether avoids the use of radioisotopes, so as simplify operation and licensing, and eliminate the possibility of diversion of such radioisotopes for illegal purposes.

Prior X-ray sources have not achieved a position of dominance due to the fact that although they can easily achieve higher energies, they have heretofore been unable to economically achieve the fluence of gamma sources. A need exists, therefore, for irradiation apparatus that can simultaneously achieve both the high energy and fluence necessary for practical sterilization, decontamination, and environmental remediation applications.

BRIEF SUMMARY OF THE INVENTION

In a preferred form, the invention provides an apparatus for Flash X-ray irradiation of material, referred to in this description as a Flash X-ray Irradiator (FXI). The FXI includes a Flash X-ray source comprised of an electron gun and an anode. The electron gun comprises a field emission cold cathode having an electron emitting surface, and a grid for controlling electron flow from the cathode to the anode. The anode has an electron-receiving main surface and an X-ray emitting, oppositely facing main surface. The X-ray emitting surface emits X-radiation into an irradiation volume. The X-ray emitting surface of the anode has orthogonally oriented first and second dimensions of greater than 2 millimeters each. A high voltage pulse power supply powers the Flash X-ray source. The electron gun, anode and high voltage pulse-power supply are so constructed as to create sufficient X-radiation in said irradiation volume to achieve a desired level of irradiation of material in said volume.

In a preferred form, the FXI according to the invention provides a means for rapidly irradiating large volumes of materials.

The Flash X-ray Irradiator has a maximum energy output below the threshold of $^{60}$Cobalt, so as to avoid the problem of inducing radioactivity in material being irradiated. The Flash X-ray Irradiator also avoids the use of radioisotopes, as in the prior art use of $^{60}$Cobalt for irradiation, so as simplify operation and licensing, and eliminate the possibility of diversion of such radioisotopes for illegal purposes.

Unlike conventional X-ray sources, the Flash X-ray Irradiator can simultaneously achieve both the high energy and fluence necessary for practical sterilization, decontamination, and environmental remediation applications. It can also be used for various manufacturing processes.

BRIEF DESCRIPTION OF THE DRAWING

In the drawing figures, in which like reference numerals refer to like parts:

FIG. 2 shows a cross-sectional view of the planar version of the Flash X-ray Irradiator.

DETAILED DESCRIPTION OF THE INVENTION

For convenience, a list of drawing numbers and associated parts for FIGS. 1-9 can be found near the end of this detailed description of the invention.

X-Ray Generation Process

Figure 1:
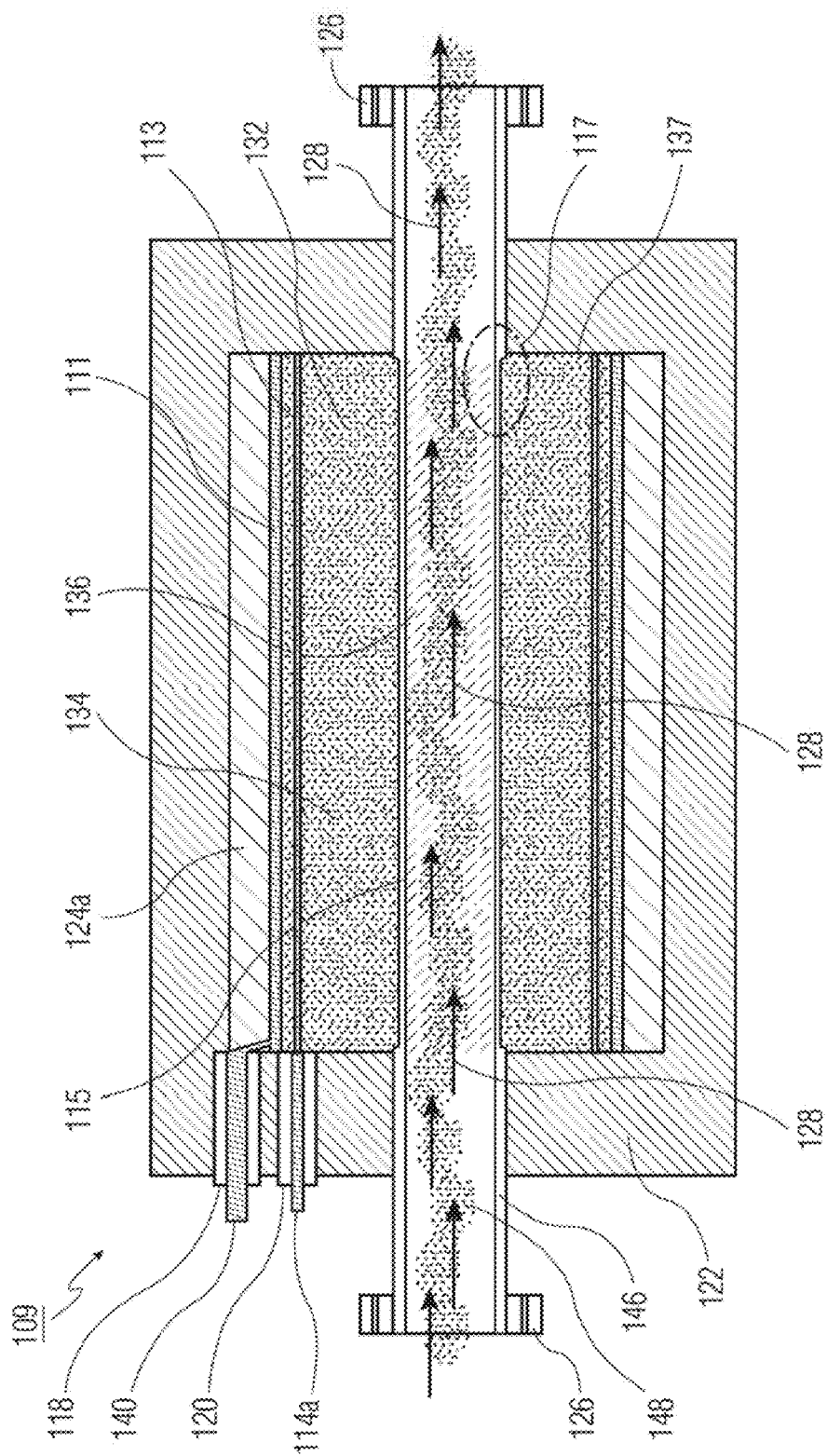
FIG. 1 shows a cross-sectional view of the cylindrical version of the Flash X-Ray Irradiator, with cross hatching omitted for various parts such as the anode.

FIGS. 1 and 2 show two different embodiments of a Flash X-Ray Irradiator (FXI). An FXI is generally a transmission type X-ray tube. It is differentiated from the prior art by several features. The first is its electron gun, which, in FIG. 1, comprises a cathode 111 and a grid 113, and in FIG. 2 comprises a cathode 112 and a grid 114. These electron guns can achieve current densities up to 80,000 Amps/cm² in the pulse mode, which ultimately result in high levels of irradiation. For instance, the FXI can achieve high energy of typically 0.1-5 MeV, a high beam current of typically 50 KiloAmp-1 MegaAmp pulses, a high fluence of typically 16 KiloGrey/pulse, and a repetition rate typically up to 100 Hz.

Figure 2A:
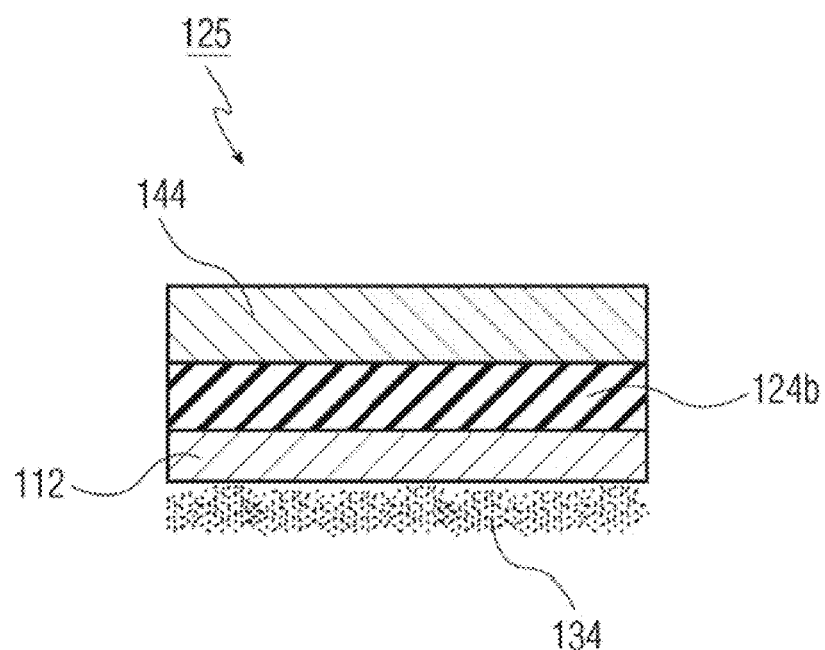
FIG. 2A shows a detail view of the circled region 125 in FIG. 2 which is modified to include a supplementary energy storage capacitor.

The Flash X-ray Irradiator 109 of FIG. 1 may advantageously include a supplementary energy storage capacitor 124a which would be coaxially wound around the cathode 111. This allows local storage of substantially greater amounts of energy without changing the physical size of the Flash X-ray Irradiator 109. Similarly, a planar implementation of a supplementary energy storage capacitor may be advantageously incorporated in the planar Flash X-ray Irradiator 110. With reference to FIG. 2A, which is modified to include a supplementary storage capacitor 124b between cathode support 144 and the cathode 112, for the same purpose as the supplementary storage capacitor 124a of FIG. 1.

Figure 3:
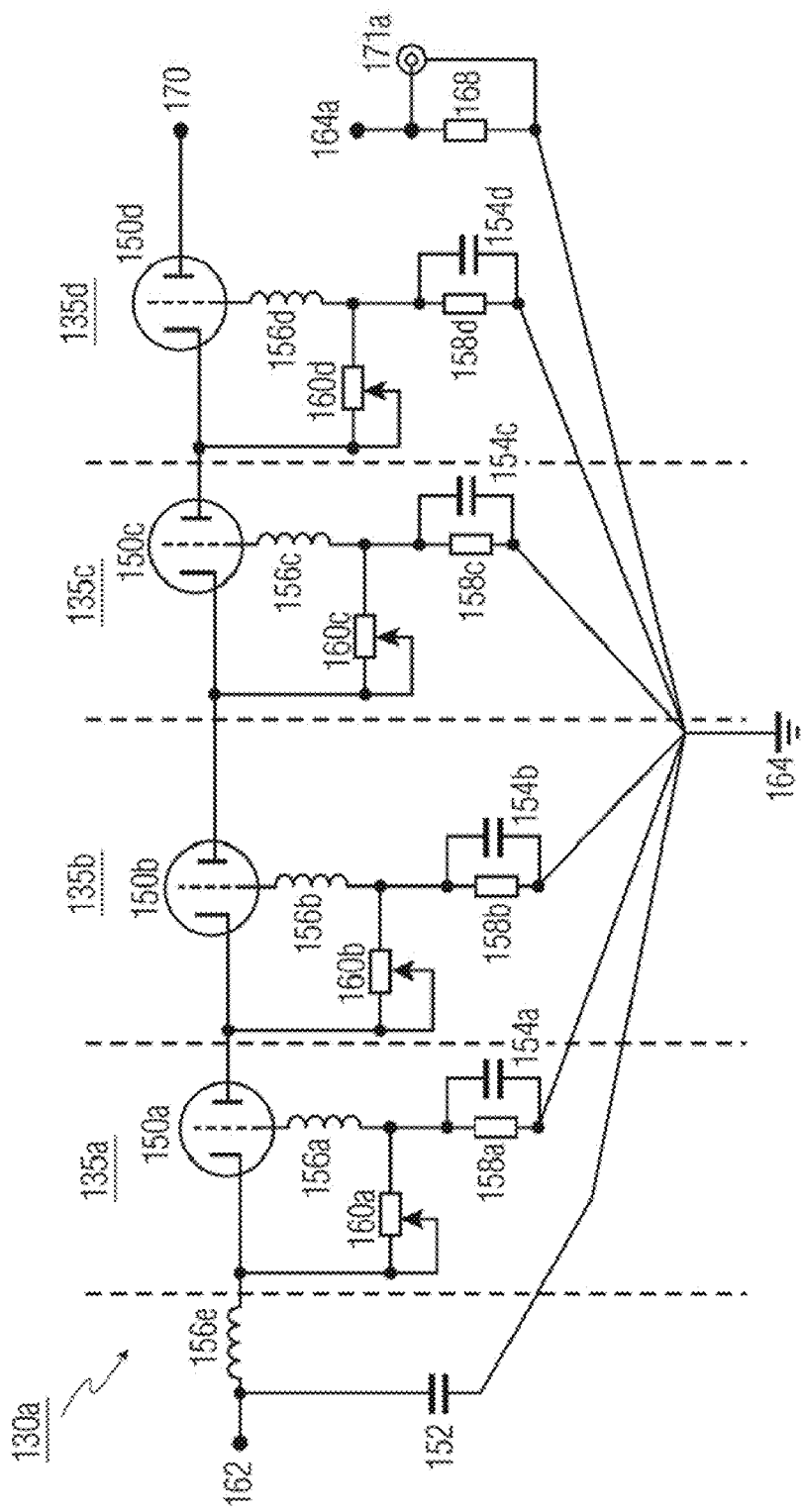
FIG. 3 shows a schematic diagram of a cascade voltage amplifier used a high voltage pulse power supply.
Figure 4A:
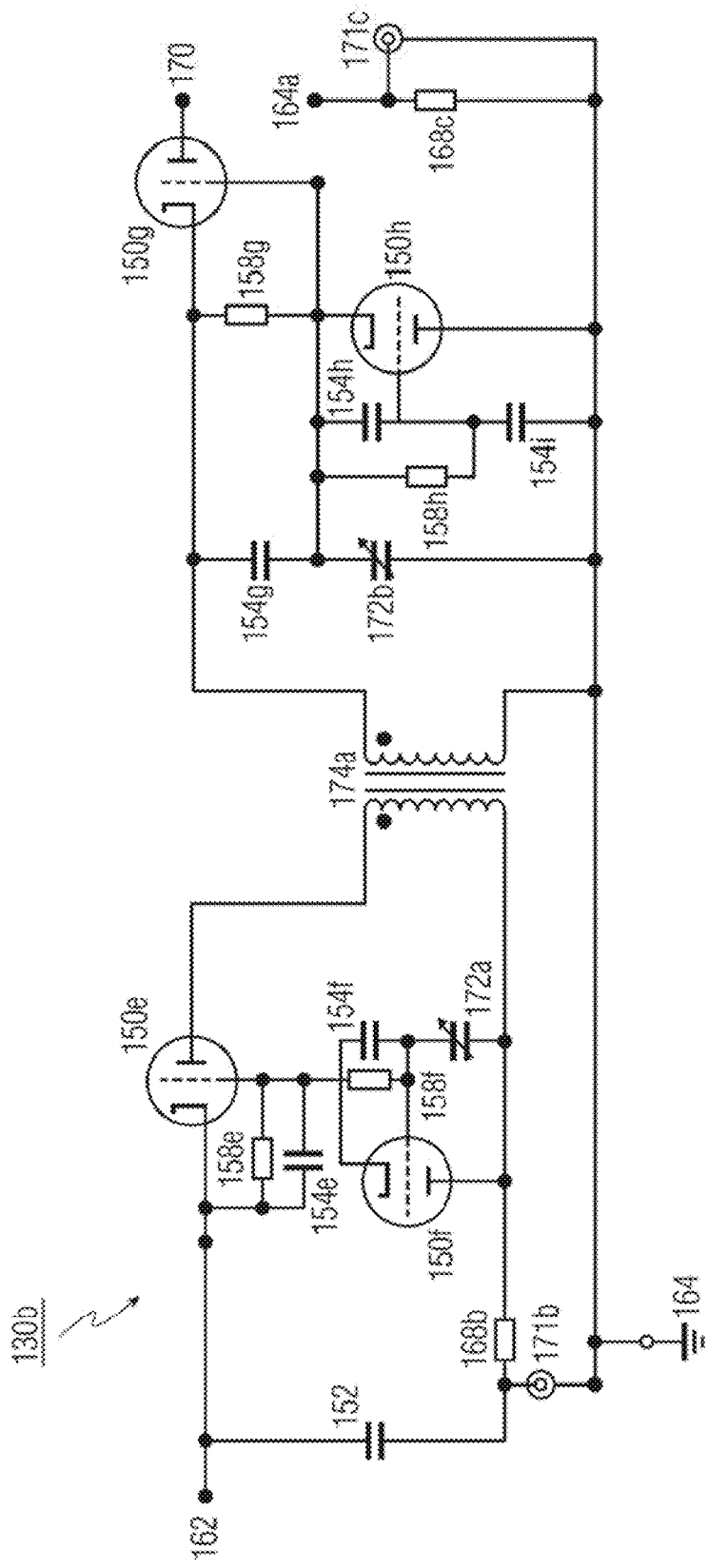
FIG. 4A shows a schematic diagram of a two-stage asynchronous pulse modulator used a high voltage pulse power supply.
Figure 4B:
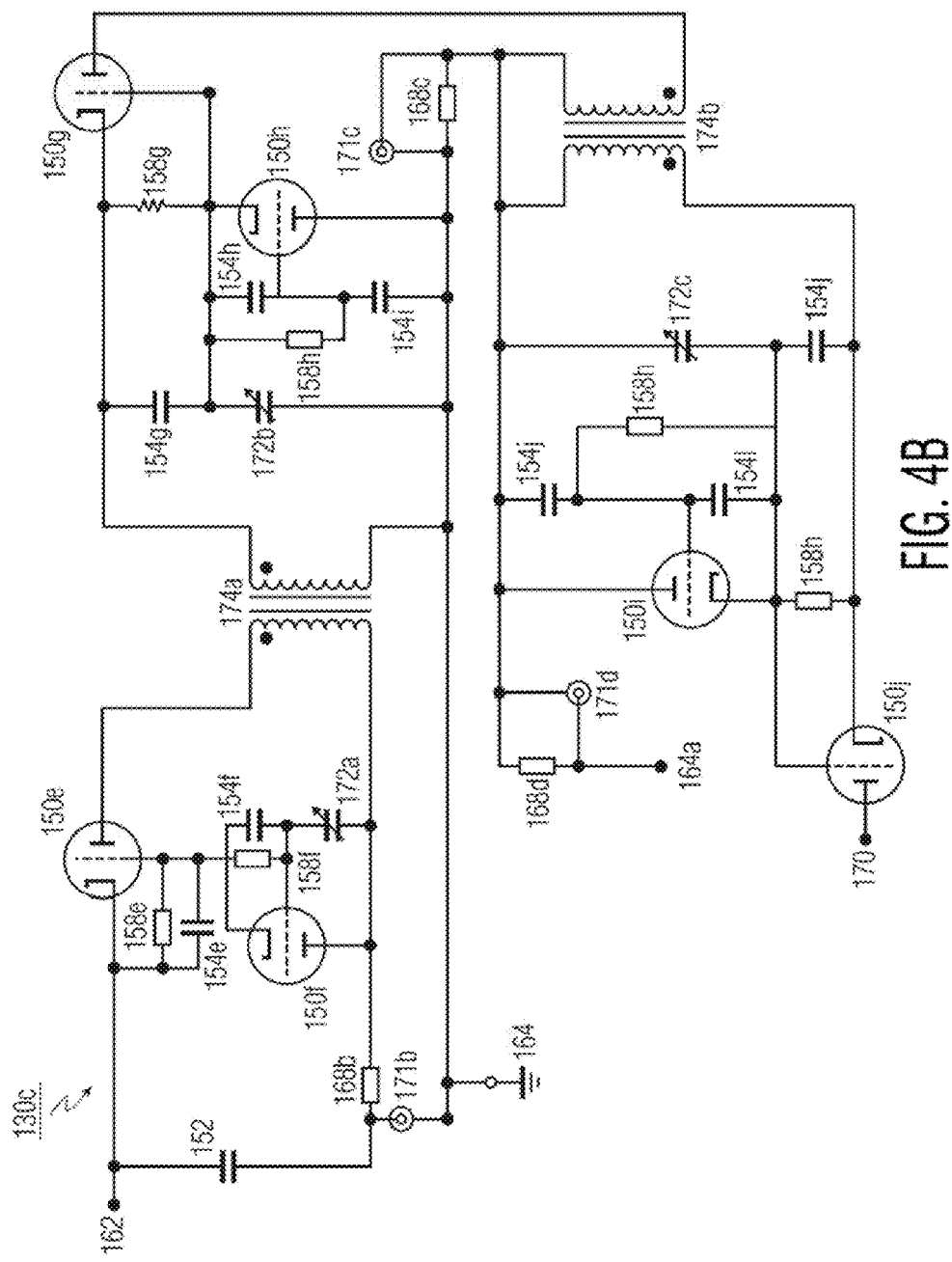
FIG. 4B shows a schematic diagram of a three-stage asynchronous pulse modulator used a high voltage pulse power supply.

Referring to both FIGS. 1 and 2, in operation, the cathode 111 or 112 is charged by the power supply 130a or 130b or 130c of FIG. 3 or 4A or 4B, respectively. A bias resistor (not shown) is connected between the cathode 111 or 112 and the grid 113 or 114 and is used to create a voltage on the grid so that the tube is normally in a standoff condition (not conducting). When a control signal of ground potential is applied to the grid, it releases control of the cathode and the cathode discharges. Electrons then travel from the cathode to the anode 115 or 116. When they strike the anode, they create Bremsstrahlung X-radiation. Bremsstrahlung is German for "braking radiation" and is created when electrons 134 with a potential in excess of 23 kiloVolts are suddenly stopped, in this case by striking the anode. When they hit the anode, a mixture of X-radiation 136 and secondary electrons (not shown) are liberated from an X-ray emitting surface of the anode in an isotropic fashion. Since the anode is thin in comparison to the penetration depth of the incident electrons, there is a preponderance of X-radiation transmitted from an electrode-receiving surface of the anode, through the anode, to an irradiation volume beyond.

Referring to both FIGS. 1 and 2, the thickness of the anode of the X-ray tube 109 or 110 is chosen to enable generation of a desired level of X-radiation. In particular, the thickness of the anode depends on a combination of factors, including the desired output voltage, the incident electron voltage, and the atomic number of the material from which it is fabricated, which number is typically over 50.

Further, the cathode and grid are fabricated to extremely tight tolerances, typically on the order of 25 microns on any dimension, even if the structure is meters long. The X-ray tube 109 or 110 is pumped to an extremely high vacuum, typically on the order of $1 \times 10^{-9}$ Torr. Although not shown in FIGS. 1 and 2, X-ray tube 109 or 110 incorporate radiation shielding for protection of persons in the vicinity of the device. The material and thickness of the radiation shield is a function of the voltage applied to the tube.

In FIG. 2, the anode 116 is preferably flat. However, the anode 116 can be formed in various shapes, such as arcuate in cross section as long as the X-ray emitting surface of the anode 116 is shaped so as to not enclose the irradiation volume. Preferably, the anode is thin, by which is meant that one dimension is much smaller than the other two orthogonal dimensions, and receives electrons from the cathode on one main surface and emits X-rays from a second, oppositely facing main surface.

For irradiating a material 148, such material must pass through the irradiation volume mentioned above. This can occur in three general ways: (1) the material can be moved through a stationary irradiation volume; (2) the irradiation volume can be moved past stationary material; or (3) both the irradiation volume and material can move simultaneously. The embodiment of FIG. 1 is particularly adapted to the first way (1), whereas the embodiment of FIG. 2 is particularly adapted to the first (1) and second (2) ways. In this connection, as mentioned above, in the embodiment of FIG. 2, the X-ray emitting surface of the anode 116 is shaped so as to not enclose the irradiation volume. In contrast, in both FIGS. 1 and 9, the irradiation volume is enclosed.

Figure 1A:
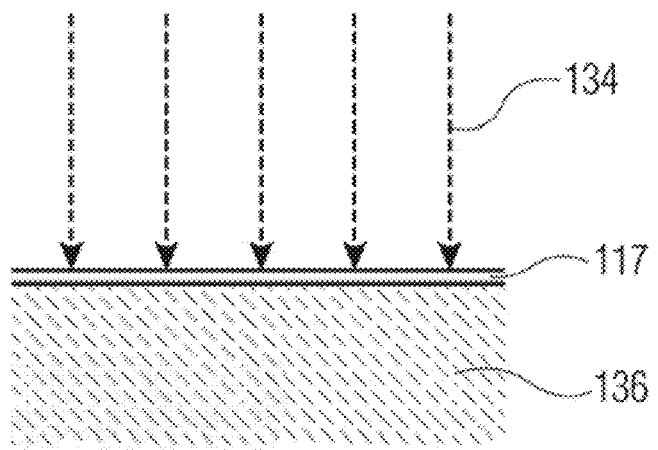
FIG. 1A shows a detail view of the circled region 117 in FIG. 1 showing the interaction of electrons with the anode to create X-rays in the transmission mode.

FIG. 1A diagrammatically shows electrons 134 that strike anode 117 on an electron-receiving surface of the anode. This results in an opposite, main X-ray emitting surface of the anode 117 emitting X-radiation 136 within the cylindrical inner volume of the anode. Similarly, in FIG. 2, electrons 134 that strike anode 116 cause a lower-shown, X-ray emitting surface of the anode to emit X-rays 136 that extend, typically below the depth shown, through an irradiation volume of material 148.

The X-ray emitting surface of the anode 115 (FIG. 1), 116 (FIG. 2) preferably has orthogonally oriented first and second dimensions of greater than 2 millimeters each. To achieve this, in the case of FIG. 1, the linear dimensions of the active portions of the cathode, grid and anode are the same; and in the case of FIG. 2, the length and width of the active portions of the cathode, grid and anode are the same.

The electron gun 111, 113 (FIG. 1) or 112, 114 (FIG. 2), anode 115 (FIG. 1) or 116 (FIG. 2) and high voltage pulse power supply 130 are so constructed as to create sufficient X-radiation in the irradiation volume mentioned above to achieve a desired level of irradiation of material 148 in that volume.

Referring to both FIGS. 1 and 2, to facilitate introduction of high voltage electrical signals through a conductive wall 137 to the cathode 111 or 112 and grid 113 or 114, vacuum-sealed insulated feedthroughs 118 and 120 are used. The anode 115 or 116 is connected to ground to complete the circuit. If needed, a cathode electrical lead (not shown) and a grid electrical lead (not shown) can be used to interconnect the vacuum-sealed insulated feedthroughs 118 and 120 to the cathode 111 or 112 and the grid 113 or 114, respectively.

Referring to both FIGS. 1 and 2 as well to other figures herein showing FXI embodiments, the material to be irradiated 148 has motion relative to the irradiation volume and constitutes flowing material 128 through the irradiation volume.

There are several critical conditions that must be met when designing a grid for a FXI. They are.
(1) The grid-cathode spacing must be constant across the length of the grid. This is usually accomplished by placing the grid under high tension or building it with a rigid structure.
(2) The number of elements in the grid must be high enough to ensure a constant and uniform electric field in the grid-cathode region.
(3) There must be no sharp edges of burs anywhere in the grid structure, individual elements can be round, flat or high aspect-ratio elliptical shapes. All edges must be fully radiused. In this context, fully radiused means that the edge in question has a radius equal to half the thickness of the material.

The actual implementation of these design rules is determined by the size of the grid being built.

Cascade Voltage Amplifier

The Cascade Voltage Amplifier 130a of FIG. 3 provides a novel way to obtain high voltage pulses for operating the Flash X-Ray Irradiators described herein, and is far more reliable and compact than the Marx generator circuit traditionally used for generating high voltage pulses. The circuit of 130a is the preferred embodiment for generating high voltage pulses for the FXI system.

In the first stage 135a, a negative high voltage power supply (not shown) is connected to input terminal 162 and is used to charge energy storage capacitor 152. Cold Cathode Field Emission Triode 150a in conjunction with inductor 156a, resistor 158a, capacitor 154a and variable resistor 160a has dual functions. They are used to both form the pulse and to amplify it by anywhere from 3 dB to 10 dB depending on the gain of the tube 150a as manufactured. The variable resistor 160a is used to set the standoff bias voltage of the tube 150a. The inductor 156a is used to block DC components from reaching the grid of tube 150a. The RC network of 158a and 154a is used to create a time constant to delay the conduction of the tube 150a.

Subsequent stages 135b, 135c and 135d are identical in function and operate as Class A amplifiers. The only differences are the voltage ratings. It is obvious that the voltage ratings of the components must be commensurate with the voltages anticipated in that stage of the circuit. Similarly, the tubes 150b, 150c and 150d are progressively larger in size to accommodate the increasing voltage.

All stages of the circuit are connected to a common RF ground 164 in accordance with good RF design practice.

The inductor 156e is used to prevent reverse voltage from reaching the charging power supply. This may be augmented by a series diode (not shown) of appropriate voltage for additional protection The current shunt 168 is an extremely low inductance low value resistor, typically in the 50 to 100 micro-Ohm range. It is necessary to apply a skin depth calculation to the output of this shunt present at the jack 171a to obtain a corrected and accurate current reading. The jack 171a is of a type that supports the anticipated bandwidth of the signal generated by the current shunt 168 based on the rise time of such signal. The output signal of the current shunt 168 is typically matched to 50 Ohms impedance.

It is noted that it is possible to reach higher voltage by adding additional stages in series with the main circuit. Care must be taken to ensure that the voltage ratings and insulation designs are commensurate with the voltages encountered. It is not uncommon to put a circuit of this type in an insulating oil tank for higher reliability.

Asynchronous Pulse Modulator Design

An alternative to the Cascade Voltage Amplifier 130a of FIG. 3 is the Asynchronous Pulse Modulator 130b or 130c of FIGS. 4A and 4B. The following description of the Asynchronous Pulse Modulator refers to both FIGS. 4A and 4B. In these figures, in the first stage, a negative high voltage power supply (not shown) is connected to terminal 162. This power supply charges energy storage capacitor 152. A voltage-monitoring circuit consisting of resistor 158e, capacitor 154e, resistor 158f, capacitor 154f, variable capacitor 172a and cold cathode field emission triode 150f is used to detect the charge state of energy storage capacitor 152. This measurement is made using a capacitive voltage divider consisting is 154e, 154f and 172a. When the voltage across the divider reaches a preset limit (determined by the setting of variable capacitor 172a), Cold Cathode Field Emission Triode 150f conducts and pulls the grid of cold cathode field emission triode 150e to ground. This causes Cold Cathode Field Emission Triode 150e to go into conduction which, in turn, discharges energy storage capacitor 152 to discharge in to the primary of the pulse transformer 174a.

The second stage starts at the secondary of the pulse transformer 174a, which typically has a turns ratio in excess of 1:10. This transformer steps the voltage up to a desired value. This is detected by a second capacitive voltage divider consisting of capacitor 154g and variable capacitor 172b. As is the case with the primary stage, when the network consisting of capacitor 154g, variable resistor 172b, resistor 158h, capacitor 154i, capacitor 154h, and Cold Cathode Field Emission Triode 150h reaches a predetermined voltage, the tube 150h conducts, pulling the grid of Cold Cathode Field Emission Triode 150g to ground and causes this triode to go into conduction, allowing the pulse present from the secondary of the pulse transformer 174 to reach the output terminal.

It is noted that resistors 158e and 159g are bias resistors used to keep their respective Cold Cathode Field Emission Triodes 150e and 150g in a standoff state in until triggered by the Cold Cathode Field Emission Triodes 158f and 158h respectively.

The current shunt 168c is a extremely low inductance low value resistor, typically in the 50 to 100 micro-Ohm range. It is necessary to apply a skin depth calculation to the output of this shunt(s) present at the jack(s) 171b or 171c to obtain a corrected and accurate current reading.

It is possible to reach higher voltage by adding additional secondary stages in series with the main circuit as shown in FIG. 4B. In the Asynchronous Pulse Modulator of FIG. 4B, stages are separated by pulse transformers 174a and 174b. The additional stage following transformer 174b is the same as the stage between transformers 174a and 174b other than voltage ratings of components. Care must be taken to ensure that the voltage ratings and insulation designs are commensurate with the voltages encountered. It is not uncommon to put a circuit of this type in an insulating oil tank for higher reliability.

Mobile Cylindrical Irradiator System

Figure 5:
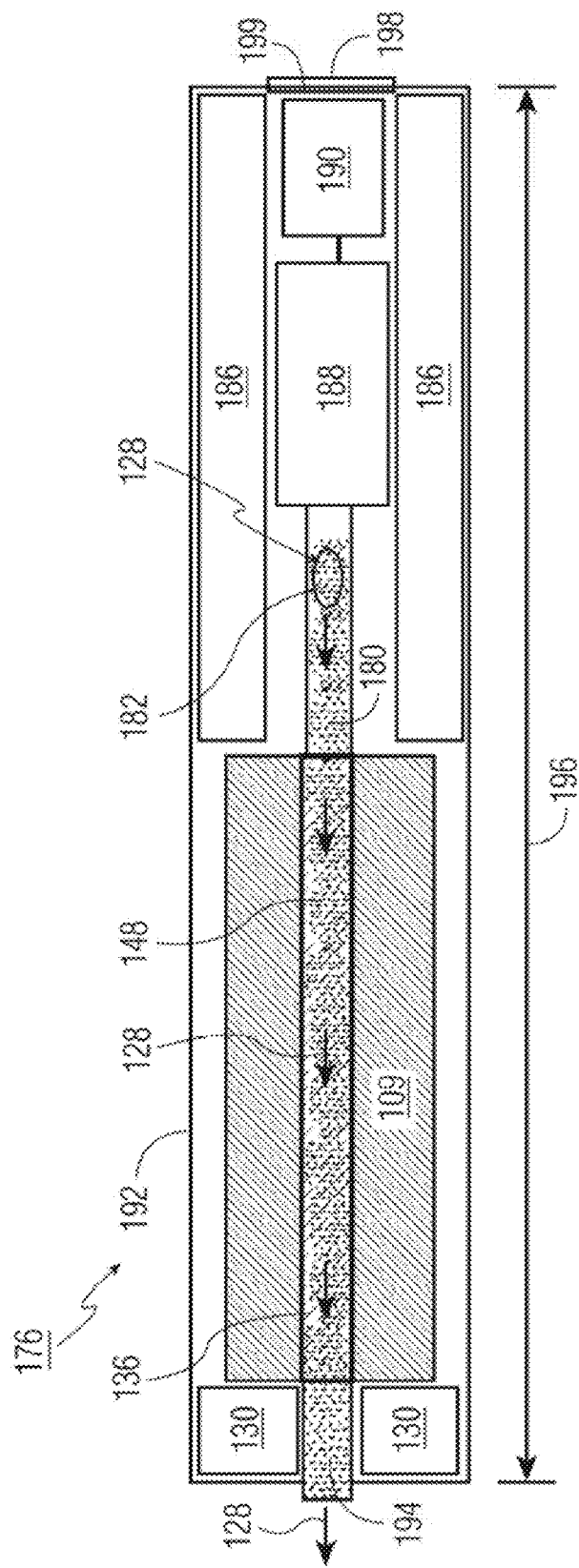
FIG. 5 shows an upper plan view in diagrammatic form of a cylindrical Flash X-ray Irradiator mounted in a standard shipping container and integrated with a turbo-jet engine powered generator and a high voltage power supply.

As illustrated in FIG. 5, a practical configuration 176 of the Flash X-Ray Irradiator places a cylindrical FXI 109 in a standard shipping container 192 with all its support equipment integrated.

In the preferred embodiment, a small turbo-jet engine 188 is mounted to the floor of the container 192. The rotating shaft of the engine 188 is connected to an electrical generator 190 having an internal gearbox speed reducer. This configuration is well-known in the electric utility industry as a means for generating power to compensate for peak power surges. The exhaust of turbo-jet engine 188 is connected to a Venturi vacuum pump 180, which is, in turn connected to the input port of the FXI 109. This configuration of engine 188, pump 180 and generator 190 makes use of both the motive power of the pump for running the generator and of the exhaust of the pump to power a Venturi vacuum pump. Fuel tanks 186 provide a local source of fuel to allow independent operation for some number of hours, which depends on the size of the jet engine and the fuel tanks.

The material to be irradiated 148 is drawn by suction into the Venturi inlet port 182. This flowing material 128 passes through the device 109 and is exposed to high-intensity X-rays 136 in the interior space of the FXI 109 and then exhausted through the output port 194. The material 148 may be of any form which will flow through a pipe. A high voltage power supply 130a, 130b or 130c etc., provides the necessary operating energy for the FXI 109. The high voltage power supply is powered by the output of the electrical generator 190.

The air inlet 198 draws in outside air and flows it over the generator 190 to cool said generator 190 prior to this air entering the air inlet 198 of the turbo-jet engine 188. This arrangement promotes energy efficiency in operating the FXI. There is an air filter 199 located in the air inlet 198 to keep airborne dirt from entering the turbo-jet engine 188 and generator 190.

Because the configuration 176 is mounted in a standard shipping container 192, it can be transported by tractor trailer, ship or air with great ease.

Irradiator for Mail-Receiving Device

Figure 6:
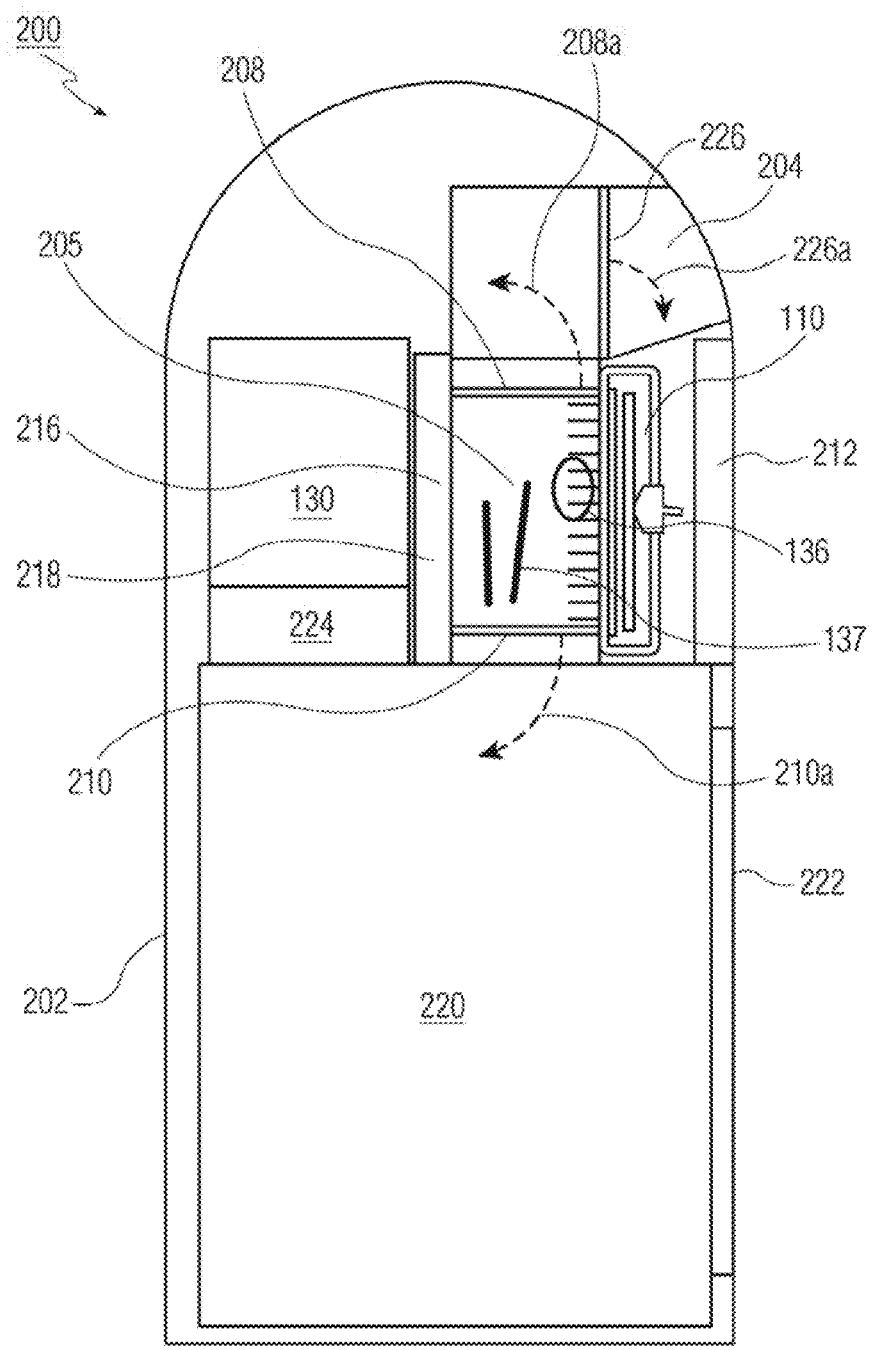
FIG. 6 shows a cross-sectional view from the left side of a planar Flash X-ray Irradiator integrated into a postal mailbox, with various thin parts shown as single lines and with cross-hatching omitted on various surfaces.

As illustrated in FIG. 6, a practical configuration 200 of the Flash X-Ray Irradiator places a FXI 110 of FIG. 2 in a mail-receiving device. In use, a person opens door 226 as shown by dashed-line arrow 226a and places some mail or other items 137 in the inlet chute 204. When the inlet door 226 closes, the upper door 208 to the irradiation chamber 205 opens as shown by dashed-line arrow 208a and the mail 137 drops into the irradiation chamber 205, and then the upper door 208 closes. The X-ray tube 110 turns on and saturates the mail 137 with high energy X-ray radiation such as that circled at 136. A dosage monitor 218 embedded in the rear wall of the chamber detects the irradiation 136, and when the irradiation has reached a satisfactory level, shuts off the X-ray tube 110. The lower door 210 to the irradiation chamber 205 then opens as shown by dashed-line arrow 210a and the sterilized mail 137 drops into the storage bin 220 below to await collection by the postal carrier. The lower door 210 then closes, and the configuration 200 resets for the next use.

The upper door 208 is hinged and opens upward, while the lower door 210 is hinged and opens downward by actuators (not shown). There are seals on both the upper door 208 and the lower door 210 which ensure an air-tight seal when the door is closed, to prevent biological contaminants from entering the storage bin 220. The storage bin may optionally be under slight positive pressure provided by the pressurizer 224 to further prevent secondary contamination of the mail. The sterilized mail is removed from the large front-access door 222.

A high voltage power supply 130a etc. provides the operating voltages for the X-ray tube 110. The X-ray tube 110 and the irradiation chamber 205 are surrounded with radiation shields front shield 212, rear shield 216, left and right shields (not shown) and upper door 208 and lower door 210, which contain shielding.

The control circuitry will quarantine mail or other items 137 in the irradiation chamber 205 if a preset minimum dosage of X-rays 136 is not achieved, to prevent contamination of previously sterilized mail for any of several reasons. One such reason would be failure of the irradiation system, for any reason. Another reason is to prevent biotoxins contained in a shielded package from entering the storage bin.

The entire system may be housed in an enclosure that resembles a standard postal mailbox, vertical mail chutes as found in office and residential buildings, or mail slots as found in post offices and other locations.

Truck-Mounted FXI

Figure 7:
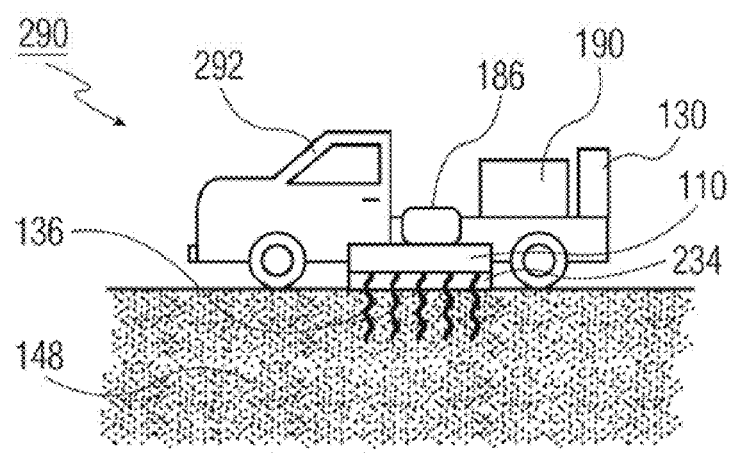
FIG. 7 shows a side-plan view in diagrammatic form of a planar Flash X-ray Irradiator mounted on the underside of a truck, with associated equipment also mounted on the truck.

A practical configuration 290 of the FXI is to mount it on the underside of a truck as shown in FIG. 7. This configuration allows rapid decontamination of underground contamination in material 148 with X-rays 136. This is particularly useful for remediation of leaking gasoline and oil tanks at gasoline filling stations, refineries and storage yards.

In FIG. 7, a preferably planar FXI 110, such as described in connection with FIG. 2 above, is mounted to the underside of a truck 292 of sufficient load-bearing capacity. The FXI 110 is mounted to allow sufficient ground clearance when the truck is driven. X-rays 136 from an X-ray emitting surface of the anode (not shown) extend, typically below the depth shown, through an irradiation volume of material 148.

To prevent stray radiation from escaping from the FXI 110, a flexible multi-layer radiation shield 234 may be mounted around the periphery of the FXI. This radiation shield is made from overlapping strips of a rubberized material that has a high content of lead, tungsten, molybdenum, or bismuth. There is a plurality of layers of such strips disposed in such a fashion that one layer covers the slight gaps between strips on the adjacent layer. A radiation shield of this design is sufficiently flexible to allow the shield to confirm to obstacles without compromising the radiation integrity of the system. The high voltage power supply 130, generator 190 and fuel tank 186 are mounted on the bed of the truck 292.

Underwater Irradiation System

Figure 8:
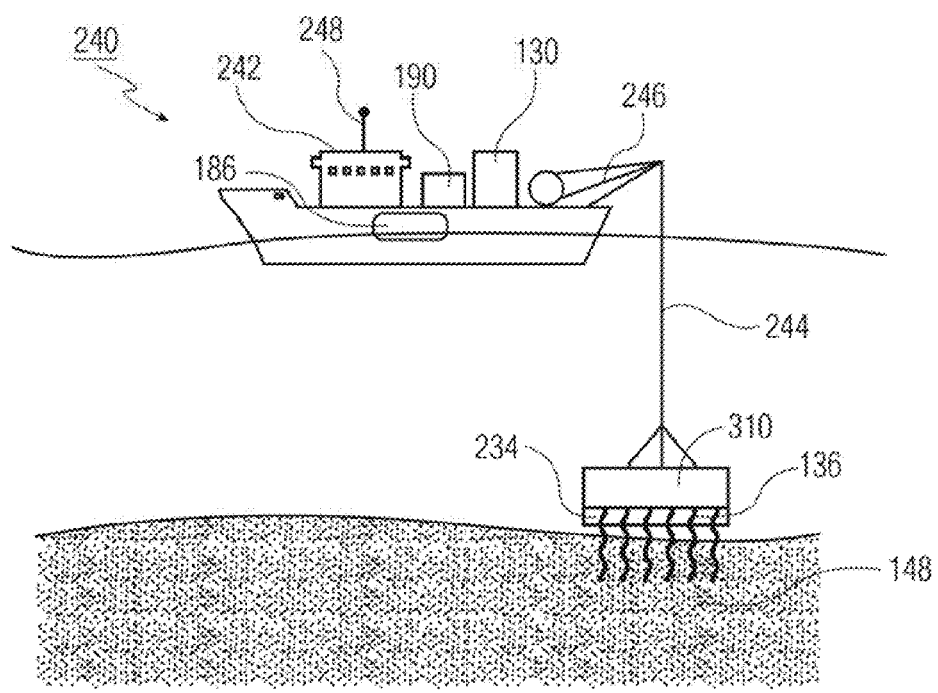
FIG. 8 shows a side-plan view in diagrammatic form of an underwater version of the planar Flash X-Ray Irradiator suspended from a crane on a boat, with associated equipment also mounted on the boat.

As shown in FIG. 8, a practical implementation of the FXI is a waterproof configuration 240 designed for operation submerged in water. This version is particularly useful in decontamination and remediation of river bottoms and coastal waters by passing X-rays into material 148 to be irradiated. FIG. 8 shows X-rays 136 from an X-ray emitting surface of the anode (not shown) extend, typically below the depth shown, through an irradiation volume of material 148.

The high intensity radiation degrades organic hydrocarbon contaminants into more benign compounds.

A boat 242 contains a generator 190, a fuel tank 186, and a high voltage power supply 130. There is a crane and winch 246 mounted on the boat to allow raising and lowering the waterproof FXI 310. A cable 244 is connected between the winch and crane 246 and the FXI 310 to raise and lower the FXI 310, including raising it entirely out of the water. The winch and crane is capable of placing the FXI 310 on the deck of the boat 242. The waterproof FXI 310 may be nearly identical to the standard planar FXI 110, except that it is has fully waterproofed electrical connections (not shown).

To prevent stray radiation from escaping, there is a flexible multi-layer radiation shield 234 mounted around the periphery of the FXI. This radiation shield is made from overlapping strips of a rubberized material that has a high content of lead, tungsten, molybdenum, or bismuth. There is a plurality of layers of such strips disposed in such a fashion that one layer covers the slight gaps between strips on the adjacent layer. A radiation shield of this design is sufficiently flexible to allow the shield to conform to obstacles without compromising the radiation integrity of the system. The rubberized material is not damaged by exposure to water.

Spherical FXI

Figure 9:
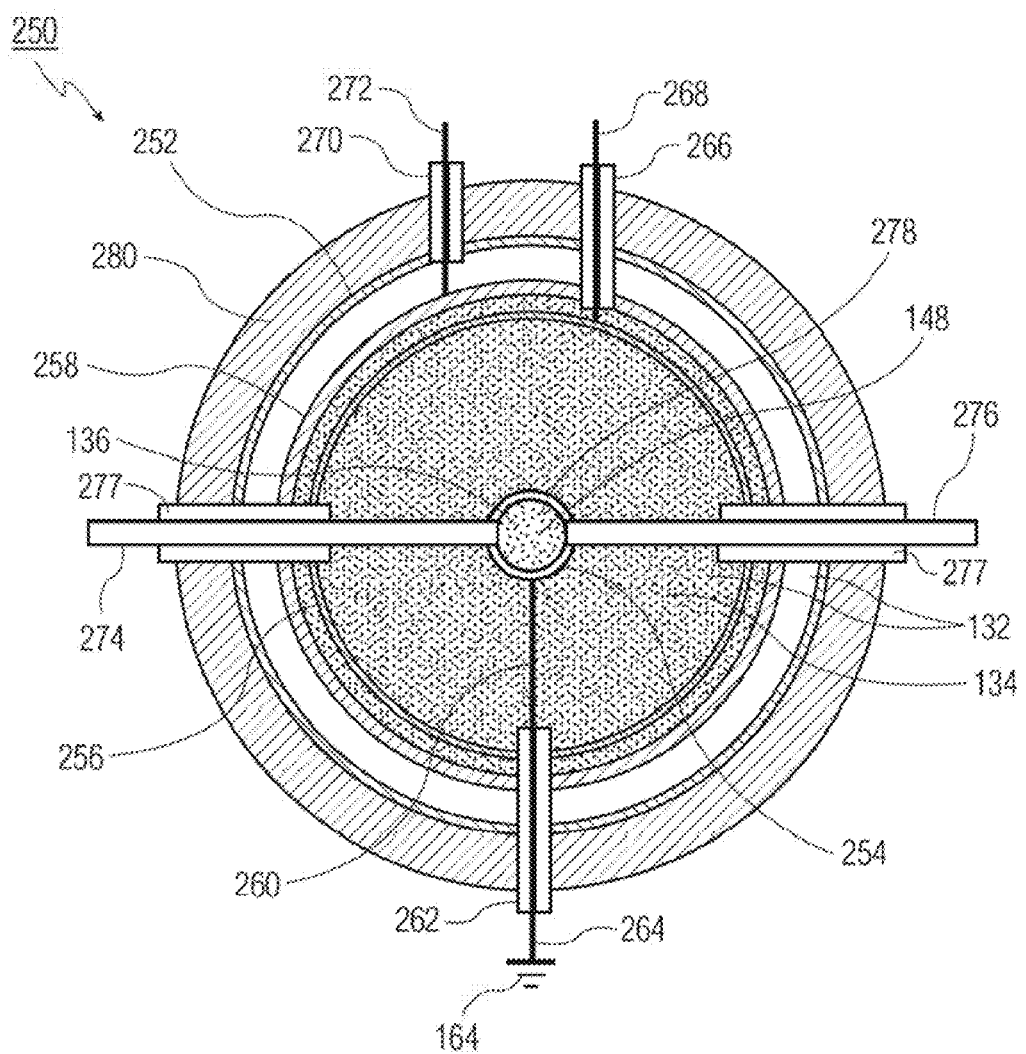
FIG. 9 shows a cross-sectional view of a spherical version of the Flash X-Ray Irradiator, with cross hatching omitted for various parts such as the anode.

It is possible to build the FXI in a spherical geometry as shown in FIG. 9. It is similar in construction to the cylindrical geometry version of the X-ray tube 109 of FIG. 1 except that it is curved in two dimensions instead of one. Operation is the same as the cylindrical FXI.

Referring to FIG. 9, the spherical FXI 250 is contained within a housing 252. There is a spherical cathode 258 which concentrically surrounds a spherical grid 256, which in turn concentrically surrounds a spherical anode 254. The interior volume of the spherical anode 254 is the irradiation volume 278. An electrical connection to the cathode 258 is provided via feedthrough 270 which contains the cathode terminal 272 that provides a connection to the cathode 258. An electrical connection is provided via feedthrough 266 for the grid 256 which contains the grid terminal 268 that provides a connection to the grid 256. An electrical connection is provided via feedthrough 262 for the anode 254 which contains the anode terminal 264 that provides a connection to the anode 254 via the internal anode lead 260. An inlet pipe 274 provides a means of introducing material 148 to be irradiated into the irradiation volume 278, and an outlet pipe 276 provides a means of egress for materials that have been irradiated.

In operation, the cathode 258 is charged by an external high voltage power supply 130a, 130b or 130c, etc. The grid 256 is connected to the cathode 258 by a bias resistor (not shown) to establish a standoff condition. When the grid terminal 264 is grounded, the electrons 134 flow to the anode 254. When the electrons strike the anode 254, they produce an X-ray flux 136 in the irradiation volume 278. The anode 254 is connected to ground 164 by internal anode lead 260 and anode terminal 264 contained within anode feedthrough 262. The entire interior volume of the housing 252 is held at a vacuum 132 of typically $1 \times 10^{-9}$ Torr.

Other Applications of Flash X-Ray Irradiator

In the case of bio-decontamination, no life-form can withstand exposure to radiation at the energies and fluences contemplated by the Flash X-ray Irradiator. An example of this is the Anthrax bacterium (*Bacillus Anthracis*). In recent years, as a result of the Anthrax attacks of 2001 in the United States, the use of high-energy radiation has become the standard for eradicating these bacteria. The Anthrax bacterium is killed with 100% reliability at a dosage of 16 KiloGreys. The high-energy radiation breaks bonds in the bacteria resulting in its destruction. These bacteria are regarded as the most resistant of all known bacteria, thus any treatment that is effective against them will also be effective against everything else.

The Flash X-ray Irradiator uses this principle in the decomposition of organic compounds. By breaking the bonds holding complex organics together, these compounds can be reduced to simpler, less hazardous and mostly benign compounds. An example of this is found in the decomposition of dioxin, which along with other higher organic compounds, cause pollution of the waterways. Dioxin is a heterocyclic organic compound with the chemical formula $C_4H_4O_2$. Exposure to high energy radiation breaks this down to $H_2O$, $CO_2$ and HCl. The Flash X-ray Irradiator can also be implemented in an underwater housing and used to decontaminate river bottoms in situ (without dredging). The quality of remediation is significantly higher as a result of the elimination of the release of plumes of contaminated material by the dredging process.

Sterilization & Environmental Remediation

The Flash X-Ray Irradiator in various configurations can be used in the areas of Decontamination and Remediation in applications such as sterilization of water, in-situ remediation of hydrocarbon contaminated soils (such as gas stations), safe decomposition of all known hydrocarbon compounds, volatile organic compounds (VOCs) polychlorinated biphenyls (PCBs), dioxins, sewage outfall treatment, stormwater runoff treatment, in-situ remediation of riverbed contamination, medical waste stream treatment, oil and chemical spill cleanup, organic dye contaminated runoff, biologically contaminated gaseous waste streams such as output air from biohazard research facilities and hospitals which may contain highly virulent species, decontamination of fish farming pens, decontamination of postal mail, decontamination of animal factory farm waste streams, sterilization of potable water, food processing waste treatment, sterilization of bilge-water of ocean-going vessels to prevent migration of alien biological species, sterilization of medical products, sterilization of pharmaceuticals, sterilization of large swimming pools, sterilization of food products, irradiation of plastics and elastomers for electronics, reformation of waste products.

The applications can be further categorized into the four major sections of 1. Hydrocarbon Remediation, 2. Decontamination, 3. Sterilization and 4. Manufacturing.

1. Hydrocarbon Remediation

Hydrocarbon contaminated soils (such as beneath gas stations and refineries): One of the largest environmental problems that he global community faces is contamination of the ground beneath gas stations, oil terminals, or any oil handling facility due to leaking tanks. Hundreds of millions of dollars are both spent and wasted in the U.S. due to the inefficient remediation techniques currently available. A portable system based on the Flash X-ray Irradiator technology is expected to be able to decompose all hydrocarbons in the soil either in situ or excavated from an average gas station in under one day. This compares favorably to the amount of time, often months to years, it currently takes to achieve the same end result. This reduction in remediation time leads to a dramatic savings in effective cost for the service stations, oil terminals or any oil handling facility. A similar situation exists with in-situ remediation of contaminated riverbed, or sea bed or lake bed of coastal waters.

Safe Decomposition of Hydrocarbon & Organic Compounds: The same technology and hardware used for hydrocarbon contaminated soils can be used to decompose all hydrocarbon compounds.

Volatile Organic Components: Volatile Organic Compounds (VOCs) represent a large regulated class of environmental contaminants. The Flash X-ray Irradiator safely decomposes VOCs rapidly and economically. This class of environmental contaminants is very large as the U.S. Environmental Protection Agency has reported at least 487 contaminants.

Polychlorinated Biphenyls: Polychlorinated Biphenyls (PCBs) are another environmental contaminant that is difficult to manage. While there has been a long-standing effort to remove these materials from the environment, the procedures are expensive and time-consuming. In many cases, the decision has been made to leave the PCBs in place as there has previously been no cost-effective method of removing and destroying them. In certain cases, Flash X-ray Irradiator technology can destroy the PCBs in situ, a capability which has never been available before.

Dioxins: Dioxin is a heterocyclic organic compound with the chemical formula $C_4H_4O_2$. Dioxins are a particularly noxious and toxic series of compounds. They are generally byproducts of other organic processes. Previous attempts to destroy dioxins by incineration have produced its own set of byproducts that are damaging the environment. Current scientific literature uses the name "dioxins" commonly for simplification to denote the chlorinated derivatives of dibenzo-p-dioxin, more precisely the polychlorinated dibenzodioxins (PCDDs). The polychlorinated dibenzodioxins, which can also be classified in the family of halogenated organic compounds (halocarbons), have been shown to bioaccumulate in humans and wildlife due to their lipophilic (the ability of a chemical compound to dissolve in fats, oils, lipids, and non-polar solvents) properties, and are known teratogens, mutagens, and carcinogens. The Flash X-ray Irradiation process will efficiently decompose these dioxins into harmless compounds and gases.

2. Decontamination

Sewage Outfall Treatment: Sewage treatment plants are not completely effective in the removal of organic and biological contaminants. Most sewage treatment plants have some form of treatment process at the end of the process cycle to address this problem. Many known technologies such as the commonly used ultraviolet treatment are energy-inefficient and maintenance-intensive and none achieve total decontamination. The sludge (sewage outfall) contaminates the area into which it is discharged. The Flash X-ray Irradiator has the capability to resolve these problems by completely sterilizing the sludge, thereby mitigating the issues associated with its disposal.

Stormwater Runoff Treatment: The U.S. Environmental Protection Agency has recently mandated that all stormwater runoff be treated to remove all biological contamination. There is currently no technology available to efficiently perform this task. The Flash X-ray Irradiator can be produced in large quantities at sufficiently low cost to allow municipalities to install this technology to remediate this problem.

Medical Waste Stream Treatment: Due to the ability of the Flash X-ray Irradiator to generate radiation fluxes in the range of 16 KiloGreys per pulse, it is practical to consider the use of this technology to sterilize waste streams from hospitals to completely eliminate any pathogens. It is anticipated that the use of this technology would eliminate the need for special handling and disposal of medical wastes.

Oil and Chemical Spill Cleanup: Traditional approaches to oil spill cleanup are relatively crude. They consist of using floating booms to contain the spill and using slow-moving boats with specialized pickup systems (skimmers) to remove the oil from the surface of the water. However, these systems are only successful if promptly applied and used on calm water. With pumping velocities of 25,000 gallons per minute which allow for cleanup, the high volume processing capacity of the cylindrical Flash X-ray Irradiator changes the paradigm of oil and chemical spill mitigation.

Organic Dye Contaminated Runoff Treatment: Factories that either produce or use organic-based dyes represent another pollution source, which in some areas of the world constitutes the predominant source of pollution. Because these dyes (mostly used in fabric coloring and printing inks) are complex hydrocarbons, they can be readily decomposed into safe compounds for disposal.

Biologically Contaminated Gaseous Waste Stream Treatment: Output air from biohazard research facilities and infectious wards in hospitals contain highly virulent species which must be killed before the air is exhausted into the atmosphere. The cylindrical version of the Flash X-ray Irradiators when coupled with a high velocity air handling system is well suited for this application. The same system used for stormwater runoff treatment and similar applications can be effectively used for this application.

Decontamination of Fish Farming Pens: A novel application for the Flash X-ray Irradiator is in sterilizing the water in fish farming pens. The high throughput of the Flash X-ray Irradiator coupled with its high sterilizing efficiency offers a means to rescue this industry. Norway has had to cut down its production of farmed salmon due to contamination of the fish. The Flash X-ray Irradiator coupled with an efficient water pumping system will be effective in removing the biological contaminants, allowing farmers to produce a higher yield of healthy fish.

Decontamination of Postal Mail: Following the U.S. cases of Anthrax in 2001 and 2002, it was realized that postal mail was extremely vulnerable to bio-contamination. Many institutions in the U.S. have already installed irradiation systems to decontaminate their incoming postal mail. To achieve decontamination of mail, the planar Flash X-ray Irradiator configuration, a flat panel irradiator mounted over a conveyor belt, works best. The panel can be several meters wide and the belt speed is high. This application is similar to the food irradiation application, in that the significantly higher beam current of the Flash X-ray Irradiation technology will allow substantially higher throughput and lower operating costs. There are many more institutions that would benefit from adding this technology such as banks, credit card companies, insurance companies, or other organizations that handle large volumes of incoming mail.

Decontamination of Animal Factory Farm Waste Streams: A single large pig farm with 500,000 pigs produces more waste on a daily basis than the population of 10 million on the entire island of Manhattan in New York. At one time, factory farms were located in remote areas and the waste was either stored in large retention ponds or injected into the ground. The expansion of urban areas has begun to encroach on the areas where factory farms are located. The odors associated with these farms are substantial and the health risks are enormous. The potential for groundwater contamination by deadly pathogens being introduced into the groundwater is an actual threat. Many phosphate contaminated waste streams can be treated using the Flash X-ray Irradiator. Both types of the Flash X-ray Irradiation system, cylindrical and planar, will be useful in this field. The cylindrical irradiator will be used in permanent and portable installations.

3. Sterilization

Sterilization of Potable Water: Providing clean, fresh water is a critical issue in every country. The Flash X-ray Irradiation technology can sterilize water more effectively than currently-used chlorine and ultraviolet remediation technologies. Its ability to process large volumes of water and its low maintenance requirements make it the preferred technology for potable water treatment. The pipe that the water flows through during the irradiation cycle is a stainless shell thus complying with all regulatory requirements for potable water systems. The Flash X-ray Irradiator is available in standard sizes up to 1 meter internal diameter. Larger sizes can be accommodated.

Food Processing: Commercial irradiation of food products is already a well-established process. The Flash X-ray Irradiator can effectively penetrate this market due to its lower operating cost and higher throughput. For example, current systems using electron beams or X-rays can generate a beam current of about 2 Amperes. By comparison, the similarly-sized Flash X-ray Irradiator system will produce a beam current in excess of 20,000 Amperes. This means that the time required to achieve the same level of processing is cut by a factor of 10,000. This factor, when combined with the significantly higher reliability, will solve the problem at a greatly reduced cost.

Sterilization of Bilgewater of Ocean-going Vessels: In order to prevent and treat the effects of migration of foreign biological species into the territorial waters of any other country, the Flash X-ray Irradiator can be installed on cargo ships. This is an area that has received much attention in the environmental community. Cargo ships using seawater for ballast are required, in the U.S. and many other countries, to decontaminate ballast water prior to dumping at the destination port. Dumping of contaminated ballast has been proven to introduce harmful alien species of flora and fauna into destinations waters, with devastating results. So, there is a great need for the FXI technology.

Sterilization of Medical Products: Surgical instruments, bandages, sutures, medical procedure kits and a wide array of other medical products which are routinely sterilized by exposure to $^{60}$Cobalt can be treated with the Flash X-ray Irradiator. The systems for sterilization with $^{60}$Cobalt are expensive and cumbersome. The Flash X-ray Irradiator can replace these systems with both lower installed and operating costs and with equal sterilization efficiency.

Sterilization of Pharmaceuticals: The same techniques for sterilization of medical products and other bio-decontamination applications can be applied to pharmaceutical production. A wide array of pharmaceutical products is currently sterilized using various radiation and electron-beam sources. In this application, the Flash X-ray Irradiator offers higher throughput and lower operating and installed costs than existing technologies.

Sterilization of Large Swimming Pools: Swimming pools are subject to a large number of bio-contaminants including by not limited to urine, feces, blood, other bodily fluids and other random contaminants. While chlorine is traditionally used for decontamination of swimming pools, it is expensive, emits an unpleasant odor and chlorine dispensing systems require constant maintenance. Swimmers frequently find the residual smell of chlorine offensive, and bathing suits can decompose due to the acidic nature of the swimming pool water. Further, the human eye is susceptible to extreme irritation from chlorine. All of these problems can be mitigated by the use of a high throughput Flash X-ray Irradiator.

Sterilization of Food Products: The same arguments for sterilization of medical products, and other bio-decontamination applications can be applied to the processing of food products. Irradiation has been shown to increase the shelf life of products, eliminate the need for refrigeration in some products (by killing the bacteria that cause spoilage), and increase the safety of packaged foods in general. The same set of advantages applies here as in other applications: higher throughput, lower operating and installed cost.

4. Manufacturing

Irradiation of Plastics and Elastomers for Electronics: There are many applications of irradiated plastics in electronic manufacturing. The largest application is the production of "heat-shrink" tubing by X-ray radiation-induced cross-polymerization. The Flash X-ray Irradiator technology can allow significantly higher production rates while simultaneously reduce manufacturing costs.

Reformation of Waste Products: The Flash X-ray Irradiator can combat air pollution caused by combustion gases from industrial plants. Typical byproducts of the decomposition of combustion gases are sulfur dioxide ($SO_2$) and nitrous oxides ($NO_x$). The Flash X-ray Irradiator is capable of reformation of certain waste products, for instance cellulosic waste, a byproduct of paper-making, into higher order hydrocarbons.

Long-Felt but Inadequately Solved Needs

Many of the foregoing applications of the X-Ray Irradiator relate to areas of long-felt and substantial need that lack a solution comparable to that of the X-Ray Irradiator. For instance, the problems associated with using the radioisotope $^{60}$Cobalt for irradiation, as mentioned above, persist; and conventional X-ray sources lack the fluence necessary for practical sterilization, decontamination, environmental remediation and manufacturing applications.

DRAWING REFERENCE NUMBERS

The following is a list of drawing reference and associated parts for each figure, for convenience of reference:

| | | |
|---|---|---|
| FIGS. 1 and 2 | FIG. 1 | FIG. 2 |
| Flash X-ray Irradiator | 109 | 110 |
| Cathode | 111 | 112 |
| Grid | 113 | 114 |
| Grid electrical lead | 114a | |
| Anode | 115 | 116 |
| Anode Thin Section Region | 117 | |
| Cathode Feedthrough | 118 | |
| Grid feedthrough | 120 | |
| Radiation Shield | 122 | |
| Supplementary Energy Storage Capacitor | 124a | 124b |
| Circled region in FIG. 2 | | 125 |
| Pipe Flange | 126 | |
| Flowing Material | 128 | 128 |
| Power Supply | 130 | |
| Vacuum Region | 132 | |
| Electrons | 134 | |
| X-rays | 136 | |
| Housing | 137 | 138 |
| Cathode Electrical Lead | 140 | |
| Grid Electrical Lead | | 142 |
| Cathode Support | | 144 |
| Pipe | 146 | |
| Material to Be Irradiated | 148 | |
| FIG. 1A | FIG. 1A | |
| Anode | 117 | |
| Electrons | 134 | |
| X-rays | 136 | |
| FIG. 2A | FIG. 2A | |
| Modification of circled region in FIG. 2 | 125 | |
| Cathode | 112 | |
| Supplemental Energy Storage Capacitor | 124b | |
| Electrons | 134 | |
| Cathode support | 144 | |
| FIG. 3 | FIG. 3 | |
| Cascade Voltage Amplifier | 130a | |
| Cold Cathode Field Emission Triode | 150 (a, b, c, d, etc.) | |
| Energy Storage Capacitor | 152 | |
| Circuit Capacitor | 154 (a, b, c, d, etc.) | |
| Inductor | 156 | |
| Fixed Resistor | 158 (a, b, c, d, etc.) | |
| Variable Resistor | 160 (a, b, c, d, etc.) | |
| Input terminal | 162 | |
| Ground | 164 | |
| Monitored ground | 164a | |
| Current Measuring Shunt | 168 | |
| HV Output Terminal | 170 | |
| Current Shunt Output Jack | 171a | |
| FIGS. 4A and 4B | FIGS. 4A & 4B | |
| Asynchronous Pulse Modulator | 130b (FIG. 4A only) | |
| Asynchronous Pulse Modulator | 130c (FIG. 4B only) | |
| Input terminal | 162 | |
| HV Output Terminal | 170 | |
| Ground | 164 | |

-continued

| | |
|---|---|
| Monitored ground | 164a |
| Energy Storage Capacitor | 152 |
| Circuit Capacitor | 154 (a, b, c, d, etc.) |
| Variable Capacitor | 172a, 172b |
| Resistor | 158 (a, b, c, d, etc.) |
| Current Measuring Shunt | 168 |
| Pulse Transformer | 174 |
| Cold Cathode Field Emission Triode | 150 (a, b, c, d, etc.) |
| Current Shunt Output Jacks | 171 b, c, d |
| FIG. 5 | FIG. 5 |
| Vehicle-mounted configuration | 176 |
| Flash X-ray Irradiator | 178 |
| HV Power Supply | 130 ("a" or "b") |
| Venturi | 180 |
| Venturi Inlet | 182 |
| Venturi Outlet | 184 |
| Fuel Tank | 186 |
| Turbo-Jet Engine | 188 |
| Generator | 190 |
| Standard Shipping Container | 192 |
| System Output | 194 |
| Dimension | 196 |
| X-rays | 136 |
| Material Flowing through Device | 128 |
| Material to be Irradiated | 148 |
| Air Inlet | 198 |
| Air Filter | 199 |
| FIG. 6 | FIG. 6 |
| Configuration | 200 |
| Housing | 202 |
| Mail Chute Inlet | 204 |
| Irradiation Chamber | 205 |
| FXI | 206 |
| Upper Door | 208 |
| Lower Door | 210 |
| Front Shield | 212 |
| Side Shield | 214 |
| Rear Shield | 216 |
| Dosage Monitor | 218 |
| Storage Bin | 220 |
| Access Door | 222 |
| Pressurizer | 224 |
| HVPS | 130 |
| X-rays | 136 |
| Mail Being Irradiated | 137 |
| Inlet Door | 226 |
| FIG. 7 | FIG. 7 |
| Configuration | 290 |
| Truck or tracked vehicle | 292 |
| FXI | 110 |
| HVPS | 130 |
| X-rays | 136 |
| Flexible Radiation Shield | 234 |
| Generator | 190 |
| Fuel Tank | 186 |
| X-rays | 136 |
| Material to Be Irradiated | 148 |
| FIG. 8 | FIG. 8 |
| Configuration | 240 |
| Boat | 242 |
| Flexible Radiation Shield | 234 |
| Generator | 190 |
| Fuel Tank | 186 |
| FXI in Underwater Housing | 310 |
| HVPS | 130 |
| Interconnecting Cable | 244 |
| Crane & Winch | 246 |
| GPS Positioning System | 248 |
| X-rays | 136 |
| Material to Be Irradiated | 148 |
| FIG. 9 | FIG. 9 |
| Spherical FXI | 250 |
| Housing | 252 |
| Anode | 254 |
| Grid | 256 |
| Cathode | 258 |
| Internal Anode Lead | 260 |
| Anode Feedthrough | 262 |
| Anode Terminal | 264 |
| Grid Feedthrough | 266 |
| Grid Terminal | 268 |
| Cathode Feedthrough | 270 |
| Cathode Terminal | 272 |
| Material to Be Irradiated | 148 |
| Vacuum | 132 |
| Electrons | 134 |
| X-rays | 136 |
| Inlet Pipe | 274 |
| Outlet Pipe | 276 |
| Irradiation Volume | 278 |
| Radiation Shield | 280 |
| HVPS | 130 |
| Ground | 164 |

While the invention has been described with respect to specific embodiments by way of illustration, many modifications and changes will occur to those skilled in the art. It is, therefore, to be understood that the appended claims are intended to cover all such modifications and changes as fall within the true scope and spirit of the invention.

What is claimed is:

1. An apparatus for Flash X-ray irradiation of material, comprising:
  a) a Flash X-ray source comprised of an electron source and an anode;
  b) the electron source comprising a field-emission cold-cathode having an electron emitting surface, and a grid for controlling electron flow from the cathode to the anode; an electrical connection for biasing the grid;
  c) the anode having an electron-receiving main surface and an X-ray emitting, oppositely facing main surface; the X-ray emitting surface emitting X-radiation into an irradiation volume;
  d) the X-ray emitting surface of the anode having orthogonally oriented first and second dimensions of greater than 2 millimeters each;
  e) a high voltage pulse power supply for powering the Flash X-ray source;
  f) the electron source, anode and high voltage pulse power supply being so constructed as to create sufficient X-radiation in said irradiation volume to achieve a desired level of irradiation of material in said volume sufficient to induce a change in state of said material; and
  g) a vacuum housing for the cathode, grid and anode of the Flash X-ray source maintained at a high vacuum; wherein
  h) the linear dimensions of the electron-emitting surface of the cathode and the electron-receiving main surface of the anode, along the main axis of the anode, are approximately the same when the anode has an elongated cylindrical shape; or
  i) the electron-emitting surface of the cathode and the electron-receiving main surface of the anode are approximately the same size when the X-ray emitting surface of the anode is shaped without a closed loop and is shaped so as to avoid enclosing that portion of the irradiation volume normal to the foregoing surface.

2. The apparatus of claim 1, further comprising means for causing said material to pass through said irradiation volume.

3. The apparatus of claim 2, wherein:
  a) the anode has an elongated cylindrical shape with a cylindrical interior, with said irradiation volume being in the cylindrical interior of said anode; said anode being formed of a pipe having relatively thick first and second ends between which ends exists an integral, relatively thin central region containing the electron-receiving main surface;

b) the cathode has an elongated cylindrical shape;
c) the grid has a cylindrical shape and acts as a gate interposed between said cathode and said anode; and
d) the cathode is axially symmetric to and encircles said anode and said grid.

4. The apparatus of claim 3, wherein a supplementary energy storage capacitor is positioned on the side of the cathode facing away from the grid; said capacitor being located within the vacuum housing with the cathode.

5. The apparatus of claim 3, wherein:
a) the means for causing said material to pass through said irradiation volume comprises a vehicle-mounted vacuum pump; and
b) the high voltage pulse power supply has means for connection to a vehicle-mounted electrical generator.

6. The apparatus of claim 5, wherein:
c) the generator and vacuum pump are powered by a turbo-jet engine; and
d) the turbo-jet takes in air that flows over the generator so as to cool the generator.

7. The apparatus of claim 6, wherein the vacuum pump is a Venturi pump.

8. The apparatus of claim 2, wherein:
a) the X-ray emitting surface of the anode is shaped without a closed loop and is shaped so as to avoid enclosing that portion of the irradiation volume normal to the foregoing surface; and
b) the means for causing said material to pass through said irradiation volume comprises a vehicle for transporting said Flash X-ray source in such a way as to cause said irradiation volume to pass through in-situ material.

9. The apparatus of claim 8, wherein the anode, grid and cathode are flat.

10. The apparatus of claim 8, wherein the Flash X-ray source is adapted for underwater use with said X-ray emitting surface predominantly facing downward.

11. The apparatus of claim 10, wherein the means for causing said material to pass through said irradiation volume includes means for vertically and horizontally positioning said X-ray emitting surface above material to be irradiated.

12. The apparatus of claim 2, wherein:
a) the X-ray emitting surface of the anode is shaped without a closed loop and is shaped so as to avoid enclosing that portion of the irradiation volume normal to the foregoing surface; and
b) the means for causing said material to pass through said irradiation volume comprises a chute for receiving gravity-fed items; the chute containing said Flash X-ray source, having lateral sides and having alternately openable upper and lower doors for receiving the items within the irradiation volume; and the irradiation volume containing a dosage sensor for determining when a sufficient dosage of X-radiation has occurred within the irradiation volume.

13. The apparatus of claim 1, wherein;
a) the X-ray emitting surface of the anode is shaped without a closed loop and is shaped so as to avoid enclosing that portion of the irradiation volume normal to the foregoing surface; and
b) wherein a supplementary energy storage capacitor is positioned on the side of the cathode facing away from the grid; said capacitor being located within the vacuum housing with the cathode.

14. The apparatus of claim 1, wherein:
a) the anode has a spherical shape, with said irradiation volume being in a spherical interior of said anode;
b) the cathode has a spherical shape;
c) the grid has a spherical shape and acts as a gate interposed between said cathode and said anode;
d) the cathode anode and grid being concentric to and encircling said anode; and
e) the cathode, anode and grid having access ports for receiving a conduit for transport therethrough of material to be irradiated; the access ports for at least the cathode and grid being electrically insulated from said conduit.

15. The apparatus of claim 1, wherein the high voltage pulse power supply provides high voltage pulses in the range of approximately 1 to 100 nanoseconds.

16. The apparatus of claim 1, wherein the electron source is constructed in such a way that the electron source has the capability to achieve current densities of up to 80,000 Amps per square centimeter.

17. The apparatus of claim 1, wherein the high voltage pulse power supply has input and output terminals for powering the Flash X-ray source; a main current path within the power supply, between the input and output terminals, including one or more cold cathode field emission tubes.

* * * * *